(12) United States Patent
Goshayeshgar

(10) Patent No.: US 11,432,862 B2
(45) Date of Patent: **\*Sep. 6, 2022**

(54) HIGH PRESSURE BALLOON CATHETER WITH PRESSURE REGULATING VALVE

(71) Applicant: MEDTRONIC HOLDING COMPANY SÀRL, Tolochenaz (CH)

(72) Inventor: Mojan Goshayeshgar, Atherton, CA (US)

(73) Assignee: KYPHON SARL, Tolochenaz (CH)

( \* ) Notice: Subject to any disclaimer, the term of this patent is extended or adjusted under 35 U.S.C. 154(b) by 174 days.

This patent is subject to a terminal disclaimer.

(21) Appl. No.: 16/808,822

(22) Filed: Mar. 4, 2020

(65) Prior Publication Data
US 2020/0222100 A1   Jul. 16, 2020

Related U.S. Application Data

(63) Continuation of application No. 15/864,880, filed on Jan. 8, 2018, now Pat. No. 10,595,918.

(51) Int. Cl.
*A61B 17/88* (2006.01)
*A61M 25/10* (2013.01)

(52) U.S. Cl.
CPC ... *A61B 17/8855* (2013.01); *A61M 25/10184* (2013.11); *A61M 25/10185* (2013.11); *A61M 25/10186* (2013.11)

(58) Field of Classification Search
CPC ... A61B 17/88; A61B 17/885; A61B 17/8852; A61B 17/8855; A61B 17/8858; A61M 25/1002; A61M 25/1006; A61M 25/1018; A61M 25/10184; A61M 25/10185; A61M 25/10186
See application file for complete search history.

(56) References Cited

U.S. PATENT DOCUMENTS

| | | | |
|---|---|---|---|
| 3,402,717 | A | 9/1968 | Doherty |
| 3,477,438 | A | 11/1969 | Allen et al. |
| 3,675,658 | A | 7/1972 | Taylor |
| 3,919,724 | A | 11/1975 | Sanders et al. |
| 4,102,342 | A | 7/1978 | Akiyama et al. |
| 4,545,367 | A | 10/1985 | Tucci |

(Continued)

FOREIGN PATENT DOCUMENTS

EP   3260069 A1   12/2017

OTHER PUBLICATIONS

Supplementary European Search Report, European Patent Office, EP 18211520.4-1132, dated Jul. 23, 2018.

*Primary Examiner* — Eric S Gibson
(74) *Attorney, Agent, or Firm* — Sorell, Lenna & Schmidt, LLP

(57) ABSTRACT

An inflatable bone tamp includes an outer shaft defining a passageway. An inner shaft is positioned within the passageway. The inner shaft defines a lumen. A balloon has a first end coupled to the outer shaft and a second end coupled to the inner shaft such that material can flow through the lumen and into the balloon and exit the balloon through a channel between the inner and outer shafts. A valve is positioned within the channel. The valve is configured to move from a closed orientation in which the valve blocks the channel and an open orientation in which the does not block the channel. Kits, systems and methods are disclosed.

20 Claims, 20 Drawing Sheets

(56) References Cited

U.S. PATENT DOCUMENTS

| | | | |
|---|---|---|---|
| 4,793,351 A | 12/1988 | Landman et al. | |
| 5,030,210 A | 7/1991 | Alchas | |
| 5,035,705 A | 7/1991 | Burns | |
| 5,085,636 A | 2/1992 | Burns | |
| 5,112,301 A | 5/1992 | Fenton, Jr. et al. | |
| 5,217,434 A | 6/1993 | Arney | |
| 5,222,970 A | 6/1993 | Reeves | |
| 5,250,034 A | 10/1993 | Appling et al. | |
| 5,259,839 A | 11/1993 | Burns | |
| 5,304,134 A * | 4/1994 | Kraus | A61M 25/0045 604/102.02 |
| 5,380,282 A | 1/1995 | Burns | |
| 5,454,789 A | 10/1995 | Burns et al. | |
| 5,707,357 A | 1/1998 | Mikhail et al. | |
| 5,788,215 A | 8/1998 | Ryan | |
| 5,919,162 A | 7/1999 | Burns | |
| 5,968,069 A * | 10/1999 | Dusbabek | A61M 25/104 606/194 |
| 6,102,891 A | 8/2000 | Maria van Erp | |
| 6,648,854 B1 * | 11/2003 | Patterson | A61M 25/005 604/524 |
| 6,733,512 B2 | 5/2004 | McGhan | |
| 6,960,188 B2 * | 11/2005 | Jorgensen | A61M 25/1006 604/103.09 |
| 7,160,325 B2 | 1/2007 | Morningstar | |
| 7,727,228 B2 | 6/2010 | Abboud et al. | |
| 8,500,684 B2 | 8/2013 | Gardner et al. | |
| 8,591,497 B2 | 11/2013 | Pinchuk et al. | |
| 9,005,165 B2 | 4/2015 | Kaiser et al. | |
| 9,149,318 B2 * | 10/2015 | Druma | A61B 17/8858 |
| 9,668,796 B2 * | 6/2017 | Druma | A61B 17/8819 |
| 9,669,193 B2 | 6/2017 | Pinchuk et al. | |
| 10,398,484 B2 * | 9/2019 | Druma | A61B 17/8827 |
| 10,595,918 B2 * | 3/2020 | Goshayeshgar | A61B 17/8855 |
| 2006/0211983 A1 | 9/2006 | Davidson et al. | |
| 2007/0005092 A1 * | 1/2007 | Godin | A61M 25/10 606/194 |
| 2009/0299327 A1 * | 12/2009 | Tilson | A61B 17/8827 604/500 |
| 2009/0312718 A1 | 12/2009 | Onuma | |
| 2011/0118546 A1 * | 5/2011 | Dillon | A61M 25/0075 600/106 |
| 2013/0165905 A1 | 6/2013 | Pinchuk et al. | |
| 2014/0257311 A1 * | 9/2014 | Druma | A61B 17/8819 606/90 |
| 2014/0277351 A1 | 9/2014 | Ridgley et al. | |
| 2014/0364834 A1 * | 12/2014 | McCullough | A61M 25/1011 604/509 |
| 2014/0364893 A1 | 12/2014 | Pepper | |
| 2015/0224280 A1 | 8/2015 | Pinchuk et al. | |
| 2015/0342660 A1 | 12/2015 | Nash | |
| 2016/0022969 A1 * | 1/2016 | Doi | A61M 25/1029 604/99.03 |
| 2017/0246436 A1 * | 8/2017 | Bak-Boychuk | A61M 29/02 |
| 2017/0367747 A1 * | 12/2017 | Druma | A61B 17/8855 |
| 2019/0159784 A1 * | 5/2019 | Sananes | A61B 17/12104 |
| 2019/0209223 A1 * | 7/2019 | Goshayeshgar | A61B 17/8855 |
| 2020/0222100 A1 * | 7/2020 | Goshayeshgar | A61B 17/8827 |

* cited by examiner

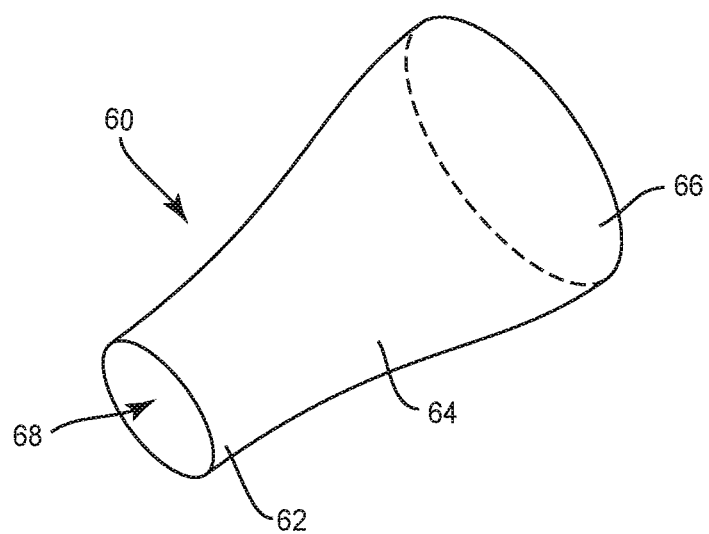
FIG. 8
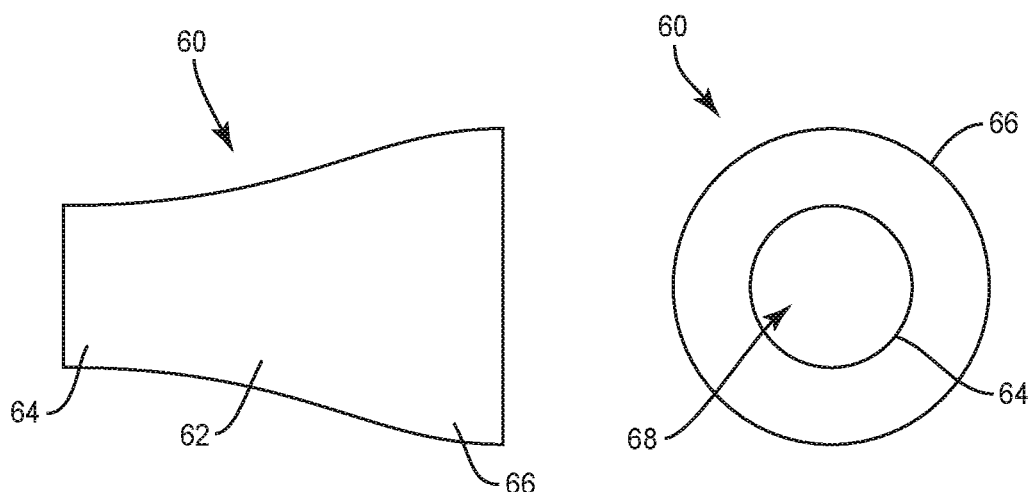
FIG. 9  FIG. 10

US 11,432,862 B2

HIGH PRESSURE BALLOON CATHETER WITH PRESSURE REGULATING VALVE

CROSS REFERENCE TO RELATED APPLICATIONS

This application is a continuation of U.S. patent application Ser. No. 15/864,880, filed on Jan. 9, 2018, which is hereby expressly incorporated herein by reference, in its entirety.

TECHNICAL FIELD

The present disclosure generally relates to medical devices for the treatment of bone disorders, and more particularly to devices and methods for treating spinal disorders, such as, for example, vertebral compression fractures.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

To adequately push the cancellous bone toward cortical walls of the vertebral body to form the cavity, the balloon is inflated at a very high pressure. Often, when the pressure within the balloon is too high, the balloon will not function properly. For example, when pressure within the balloon is too high, the balloon may form the cavity at a location other than a desired location and/or may have an incorrect size or shape. Furthermore, the high pressure used to inflate the balloon may cause the balloon to rupture while the balloon is being inflated if the pressure within the balloon exceeds the balloon's pressure limit. However, conventional spinal fracture treatment procedures lack a balloon that includes a pressure-reducing valve to vent pressure within the balloon when pressure within the balloon reaches a predetermined threshold. This disclosure describes improvements over these prior art technologies.

SUMMARY

New devices and methods are provided for the treatment of bone disorders, and more particularly devices and methods for treating spinal disorders, such as, for example, vertebral compression fractures. In some embodiments, the devices and methods may be used to dilate restrictions and blockages virtually anywhere in the body, including, for example, angioplasty/dilatation catheters and stent-delivery catheters. In some embodiments, the devices and methods may have applications as arthrectomy catheters, cryogenic catheters, drug-delivery devices, and positioning catheters. In some embodiments, an inflatable bone tamp comprises an outer shaft defining a passageway. An inner shaft is positioned within the passageway. The inner shaft defines a lumen. A balloon has a first end coupled to the outer shaft and a second end coupled to the inner shaft such that material can flow through the lumen and into the balloon and exit the balloon through a channel between the inner and outer shafts. A valve is positioned within the channel. The valve is configured to move from a closed orientation in which the valve blocks the channel and an open orientation in which the does not block the channel.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 8 is a perspective view of a component of the surgical instrument shown in FIG. 1;

FIG. 9 is a side view of a component of the surgical instrument shown in FIG. 1;

FIG. 10 is an end view of a component of the surgical instrument shown in FIG. 1;

DETAILED DESCRIPTION

Figure 1:
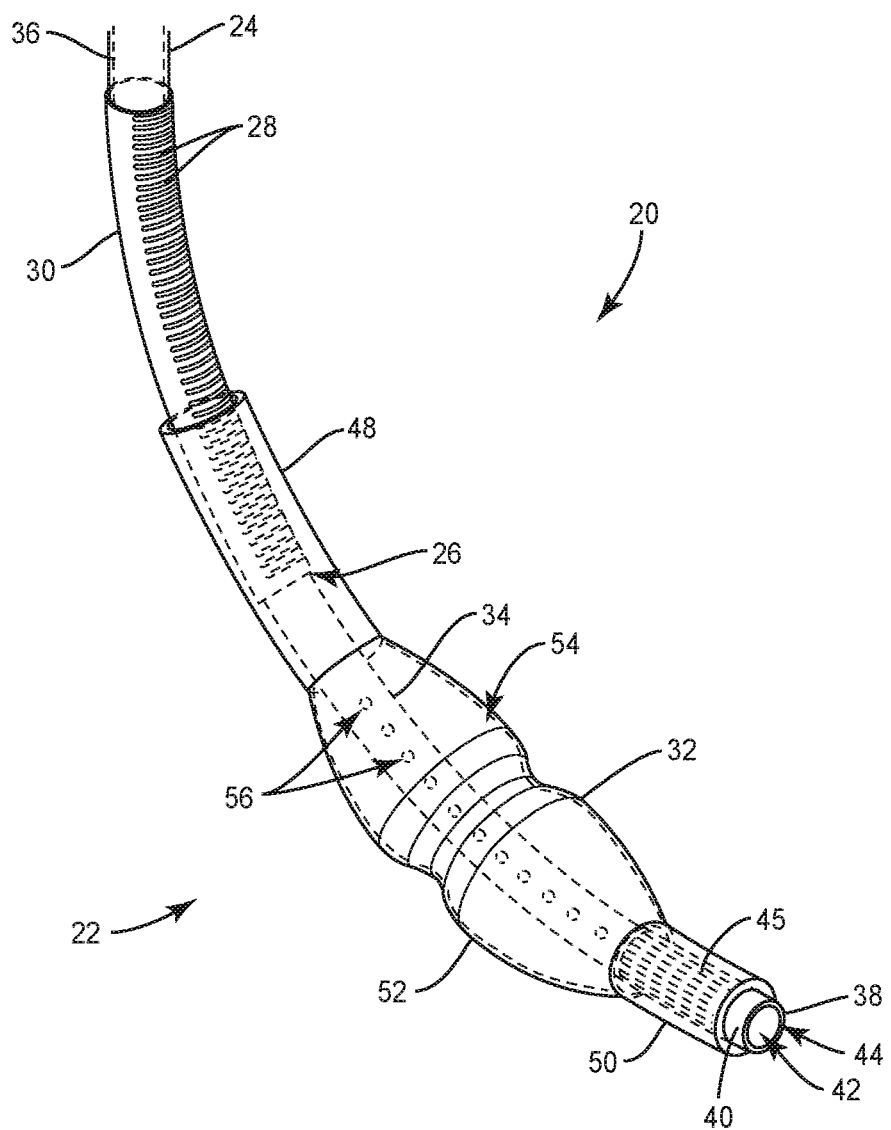
FIG. 1 is a perspective view, in part phantom, of a surgical instrument in accordance with the principles of the present disclosure.

In some embodiments, the present disclosure relates to a system that includes a curved high-pressure balloon catheter for unipedicular kyphoplasty. The system comprises a nested cannula and curved stylet to access a vertebral body through a unipedicular access. The curved stylet will create a pilot hole for positioning the curved balloon catheter through a midline of the vertebral body. The balloon catheter includes an inner shaft, such as, for example, an inner shaft made of formed or cut metallic tube or reinforced polymer tube. The balloon catheter further includes an outer shaft, a proximal design to connect to an inflation syringe and a distal high-pressure balloon.

The high-pressure balloon catheter includes a pressure-reducing valve that regulates the pressure from the balloon when pressure within the balloon reaches and/or exceeds a predetermined threshold. In some embodiments, the pressure-regulating valve is engineered of polymer with appropriate durometer. The material and geometry of the polymer valve are designed based on the pressure threshold and material properties of inflation medium and operating temperature. In some embodiments, the polymer is fused with a polymer overlay on an outer surface of the inner shaft to create a temporary dynamic seal against the inner shaft or inversely can be fused to the outer surface of the inner shaft to seal against the inner surface of the outer shaft or it can be two pieces fused to inner and outer shaft with a radial or circumferential aperture In some embodiments, the polymer is sandwiched between the inner and outer shafts to provide at least a partial seal and function as a passive pressure-reducing valve. That is, the valve is configured to move between a closed configuration in which the valve prevents material from exiting the balloon through a channel between the inner and outer shafts and an open configuration in which the valve allows the material to exit the balloon through the channel when pressure within the balloon reaches a predetermined threshold, as discussed herein.

It is envisioned that the disclosed curved balloon catheter can be used for unipedicular kyphoplasty in patients with one or more vertebral compression fractures or as an adjunctive to local tumor control interventions. In some embodiments, the balloon is specifically targeted for a vertebral body and balloon kyphoplasty so that a shape of the balloon follows an anterior wall of the vertebral body. In particular, in at least one embodiment, this will dictate a certain radius of curvature (i.e. about 25 mm) for the balloon to be positioned more anterior and passed the midline and to inflate to an optimum shape to cover the anterior ⅔ of the vertebral body for treatment of vertebral compression fractures.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" comprises any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be comprised within the invention as defined by the appended claims.

This disclosure is directed to an inflatable bone tamp, such as, for example, a balloon catheter system 20. In some embodiments, the components of balloon catheter system 20 can be fabricated from biologically acceptable materials suitable for medical applications, including metals, synthetic polymers, ceramics and bone material and/or their composites, depending on the particular application and/or preference of a medical practitioner. For example, the components of balloon catheter system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of balloon catheter system 20 may have material composites, including the above materials, to achieve various desired characteristics such as strength, rigidity, elasticity, compliance, biomechanical performance, durability and radiolucency or imaging preference. The components of balloon catheter system 20, individually or collectively, may also be fabricated from a heterogeneous material such as a combination of two or more of the above-described materials. The components of balloon catheter system 20 may be monolithically formed, integrally connected or comprise fastening elements and/or instruments, as described herein.

Balloon catheter system 20 includes an inflatable bone tamp 22 comprising an outer shaft, such as, for example a shaft 24 defining a passageway 26. In some embodiments, passageway 26 has a uniform diameter along an entire length of shaft 24. In some embodiments, passageway 26 may have various cross section configurations, such as, for example, circular, oval, oblong, triangular, rectangular, square, polygonal, irregular, uniform, non-uniform, variable, tubular and/or tapered. In some embodiments, shaft 24 may at least initially have a straight configuration, and may be bent to have a curved configuration, as discussed herein. In some embodiments, shaft 24 may be pre-bent to have a curved configuration. In some embodiments, shaft 24 may include one or a plurality of surface features, such as, for example, ridges 28 to facilitate bending of shaft 24 in a controlled manner. Adjacent ridges 28 define a channel therebetween. As shown in FIG. 1, ridges 28 are disposed along shaft 24 in a linear, serial configuration such that ridges 28 extend parallel to one another to allow shaft 24 to bend about ridges 28. In some embodiments, ridges 28 extend only along a portion of a length of shaft 24. In some embodiments, ridges 28 extend along an entire length of shaft 24. As shown in FIG. 1, ridges 28 each extend perpendicular to a length of shaft 24. However, it is envisioned that ridges 28 may be disposed at alternate orientations, relative to the length of shaft 24, such as, for example, transverse and/or other angular orientations such as acute or obtuse, co-axial and/or may be offset or staggered, depending upon, for example, the desired curvature of shaft 24.

In some embodiments, shaft 24 comprises a metallic material. In some embodiments, shaft 24 is laser cut, braided, or coiled. In some embodiments, shaft 24 is coated with a material, such as, for example, a polymer 30 configured to facilitate bonding of an inflatable member, such as, for example, a balloon 32 to shaft 24, as discussed herein. In some embodiments, polymer 30 can also encapsulate and seal the laser cut, braid, or coil to prevent material ingress or egress through a thickness of shaft 24 that is coated with polymer 30. In some embodiments, ridges 28 are formed by the metallic material. In some embodiments, ridges 28 are formed by polymer 30. In some embodiments, ridges 28 are formed by the metallic material and polymer 30. In some embodiments, only a distal portion of shaft 24 is coated with polymer 30. In some embodiments, only a portion of shaft 24 that is bonded to balloon 32 is coated with polymer 30. In some embodiments, only portions of shaft 24 that are bonded to balloon 32 and include ridges 28 are coated with polymer 30. In some embodiments, shaft 24 is coated with polymer 30 along an entire length of shaft 24. In some embodiments, shaft 24 is covered with polymer 30 along at least a portion of shaft 24. In some embodiments, polymer 30 includes a thermoplastic polymer, such as, for example, thermoplastic polyurethane (TPU). In some embodiments, polymer 30 includes an elastomeric polymer, such as, for example, a thermoplastic elastomer (TPE).

An inner shaft, such as, for example, a shaft 34 is positioned within passageway 26. Shaft 34 extends between an end 36 an opposite end 38. End 36 is positioned within passageway 26 and end 38 is positioned outside of passageway 26. In some embodiments, shaft 34 has a linear configuration such that shaft 34 is straight from end 36 to end 38. In some embodiments, shaft 34 is curved between end 36 and end 38. In some embodiments, shaft 34 is pre-bent to be curved between end 36 and end 38 such that when shaft 34 is inserted through passageway 26, shaft 34 causes shaft 24 to move from a straight configuration to a curved configuration. In some embodiments, shaft 34 is pre-bent to have a uniform radius of curvature. In some embodiments, shaft 34 is pre-bent to have a radius of curvature that varies along a length of shaft 34. In some embodiments, shaft 34 comprises a shape memory alloy, such as, for example, a super-elastic shape memory alloy. In some embodiments, shaft 34 comprises Nitinol. In some embodiments, shaft 34 is laser cut, braided, or coiled. In some embodiments, shaft 34 is coated with a material, such as, for example, a polymer 40 configured to facilitate bonding of balloon 32 to shaft 34, as discussed herein. In some embodiments, polymer 40 can also encapsulate and seal the laser cut, braid, or coil of shaft 34 to prevent material ingress or egress through a thickness of shaft 34 that is coated with polymer 40. In some embodiments, shaft 34 includes a rigid material, such as, for example, stainless steel (SST) or nickel titanium (NiTi), wherein at least a portion of shaft 34 includes one or more laser cuts to provide shaft 34 with the pre-bent shape. In some embodiments, the laser cuts are uniaxial. In some embodiments, the laser cuts are multiaxial. In some embodiments, the portion of shaft 34 that includes the laser cuts is jacketed or covered with polymer 40. In some embodiments, polymer 40 includes a thermoplastic polymer, such as, for example, thermoplastic polyurethane (TPU). In some embodiments, polymer 40 includes an elastomeric polymer, such as, for example, a thermoplastic elastomer (TPE).

Shaft 34 defines a lumen 42 configured to move an inflation material, such as, for example, air, saline, or a contrast solution into and out of balloon 32 to move balloon 32 between an uninflated configuration and an inflated configuration, as discussed herein. In some embodiments, lumen 42 has a uniform diameter along an entire length of shaft 34. In some embodiments, lumen 42 may have various cross section configurations, such as, for example, circular, oval, oblong, triangular, rectangular, square, polygonal, irregular, uniform, non-uniform, variable, tubular and/or tapered. In some embodiments, a distal end of lumen 42 is closed to prevent the inflation material from moving out of lumen 42 through a distal end of lumen and/or outside material from entering lumen 42. In some embodiments, the distal end of lumen 42 includes an opening 44 to allow an instrument, such as, for example a guide wire to be inserted through lumen 42 such that the guide wire can extend through opening 44 and into tissue in order so that bone tamp 22 can be guided along the guide wire to a target location. In some embodiments, polymer 40 includes a plurality of spaced apart grooves 45 that each extend parallel to a length of shaft 34, as shown in FIG. 1. Grooves 45 may be used to enhance fixation of cap 46 with shaft 34 and/or bonding of balloon 32 to shaft 34. In some embodiments, grooves 45 may be disposed at alternate orientations, relative to the length of shaft 34, such as, for example, transverse, perpendicular and/or other angular orientations such as acute or obtuse, co-axial and/or may be offset or staggered.

Figure 3:
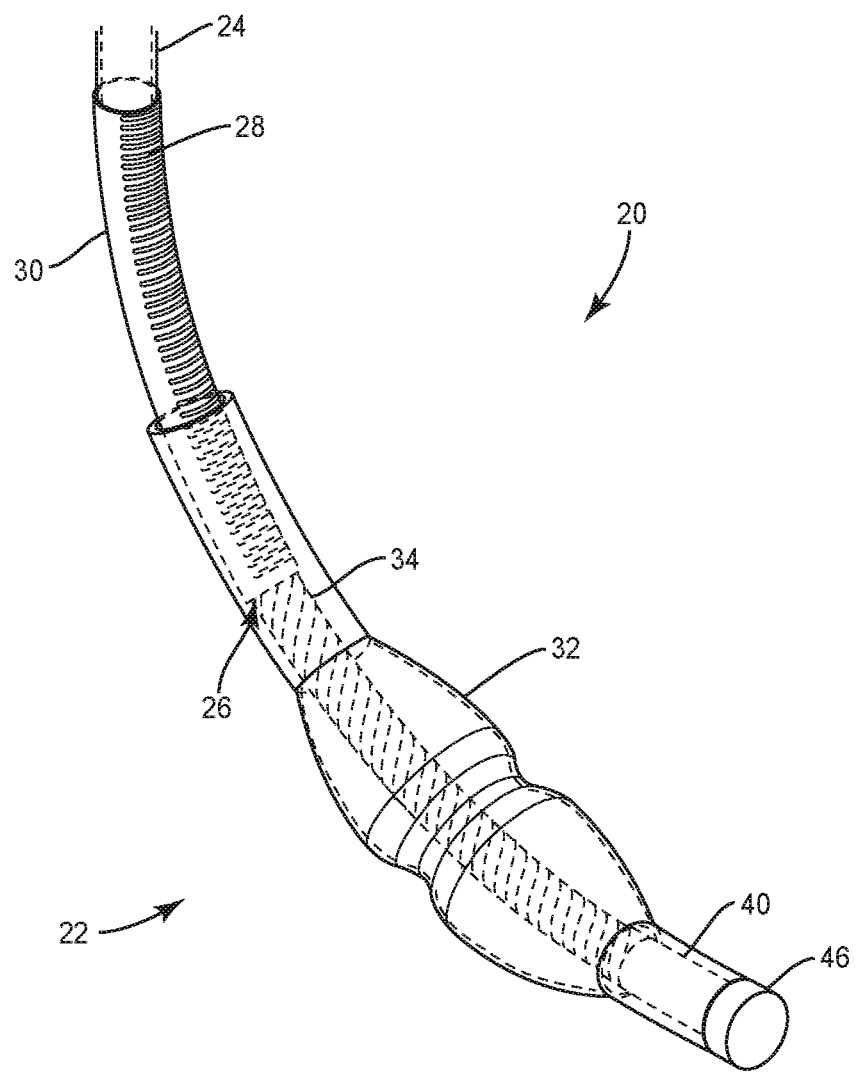
FIG. 3 is a perspective view, in part phantom, of one embodiment of the surgical instrument shown in FIG. 1.
Figure 4:
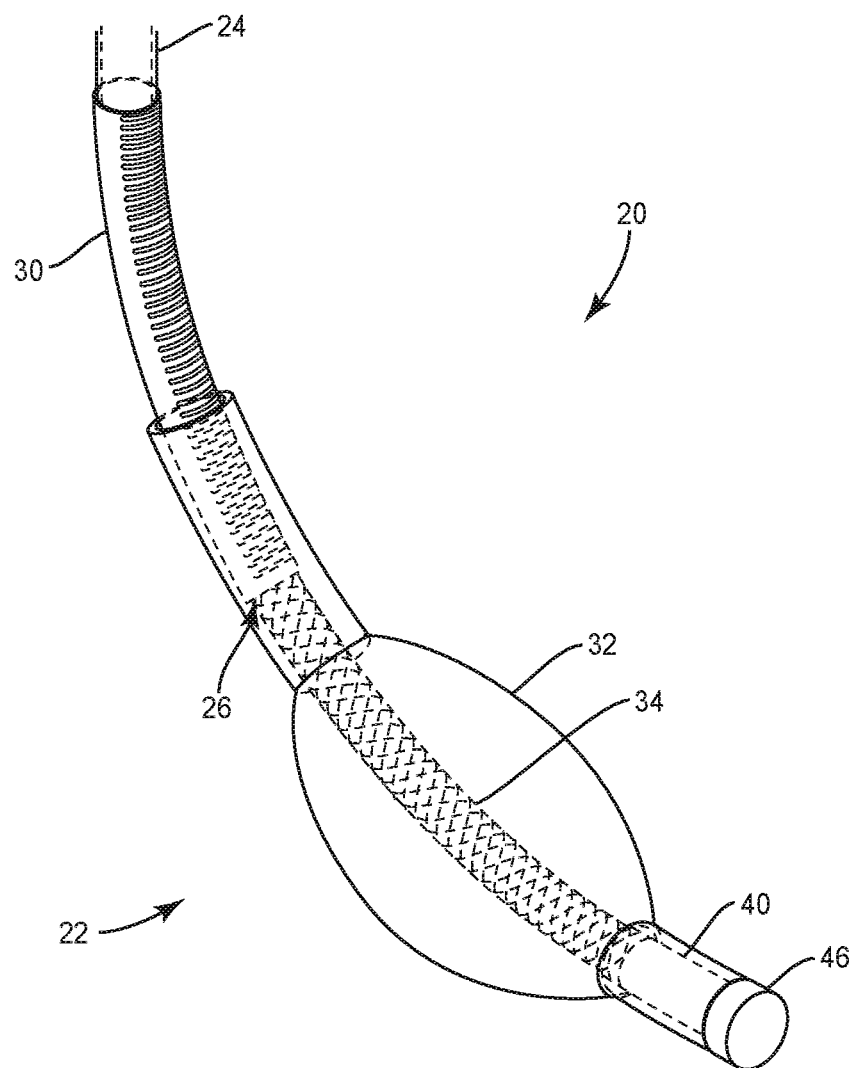
FIG. 4 is a perspective view, in part phantom, of one embodiment of the surgical instrument shown in FIG. 1.
Figure 5:
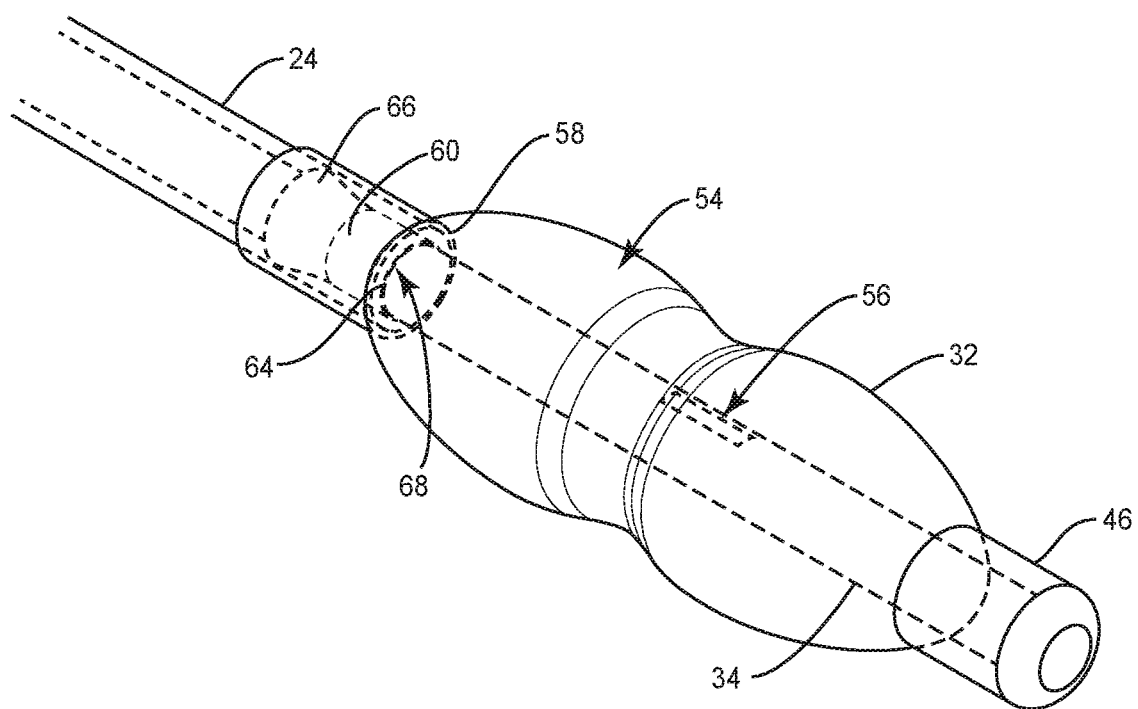
FIG. 5 is a perspective view, in part phantom, of one embodiment of the surgical instrument shown in FIG. 1.
Figure 6:
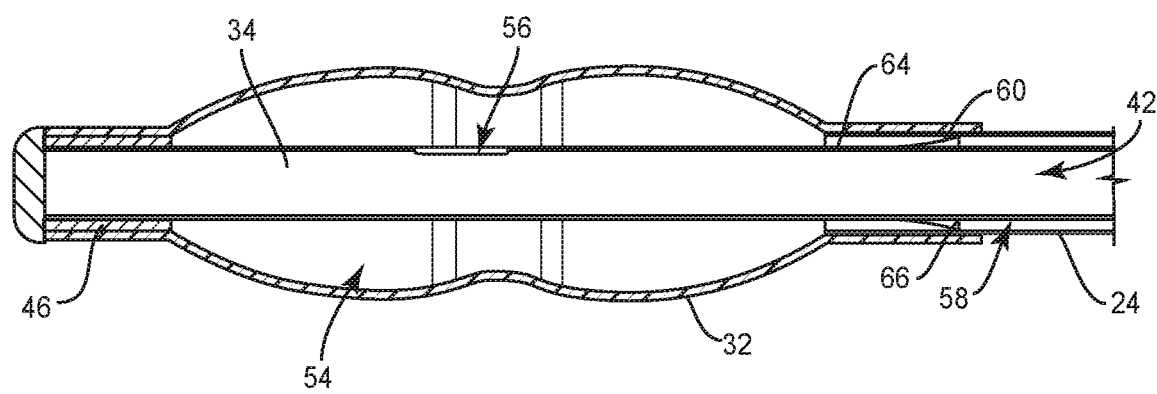
FIG. 6 is a side, cross sectional view of the surgical instrument shown in FIG. 1.
Figure 7:
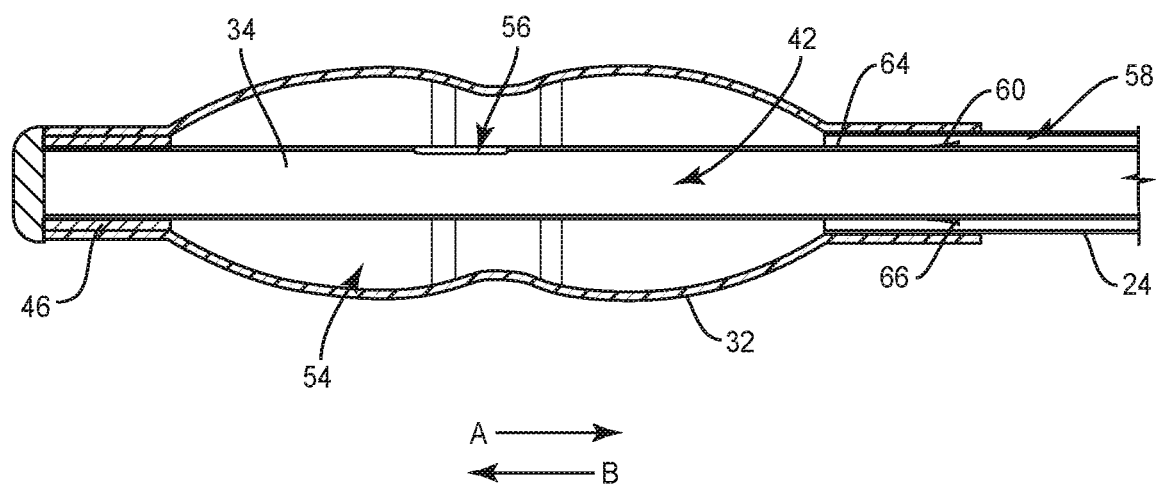
FIG. 7 is a side, cross sectional view of the surgical instrument shown in FIG. 6.

In some embodiments, bone tamp 22 may include a removable cap 46, as shown in FIGS. 3 and 4, for example. Cap 46 can be inserted onto shaft 34 such that cap 46 covers opening 44. In some embodiments, cap 46 can be variously connected with shaft 34, such as, for example, monolithic, integral connection, frictional engagement, threaded engagement, mutual grooves, screws, adhesive, nails, barbs and/or raised element. In some embodiments, a distal end of balloon 32 is bonded directly to an outer surface of shaft 34, as shown in FIGS. 1, 3 and 4. In some embodiments, the distal end of balloon 32 is bonded directly to an outer surface of cap 46 such that balloon 32 is spaced apart from the outer surface of shaft 34 by cap 46, as shown in FIGS. 5-7.

In some embodiments, balloon 32 is made from a resilient biocompatible material. In one embodiment, balloon 32 is a compliant balloon that resists stretching. In one embodiment, balloon 32 comprises polyolefin copolymer (POC), Polyurethane, Nylon. In one embodiment, balloon 32 is a non-compliant or semi-compliant balloon that stretches, at least to some degree. In one embodiment, balloon 32 comprises polyethylene terapthelate (PET). In some embodiments, balloon 32 can have various cross section configurations when balloon 32 is in the inflated configuration, such as, for example, oval, oblong, triangular, rectangular, square, polygonal, irregular, uniform, non-uniform, variable, tubular and/or tapered. In some embodiments, an outer surface of balloon 32 may have various surface configurations, such as, for example, smooth and/or surface configurations to enhance fixation with tissue, such as, for example, rough, arcuate, undulating, porous, semi-porous, dimpled, polished and/or textured.

In some embodiments, balloon 32 has a leg 48 that is bonded to polymer 30 to couple leg 48 to shaft 24. In some embodiments, leg 48 is bonded to polymer 30 using heat or an adhesive, for example. Bonding leg 48 to polymer 30 will provide a better bond than would bonding leg 48 to a portion of shaft 24 that does not include polymer 30 using heat or an adhesive. In some embodiments, balloon 32 has a leg 50 that is bonded to polymer 40 to couple leg 50 to shaft 34. In some embodiments, leg 50 is bonded to polymer 40 using heat or an adhesive, for example. Bonding leg 50 to polymer 40 will provide a better bond than would bonding leg 50 to a portion of shaft 34 that does not include polymer 40 using heat or an adhesive. Balloon 32 has a body 52 that extends from leg 48 to leg 50. That is, body 52 is positioned between leg 48 and leg 50. Body 52 includes an inner surface that defines a chamber 54.

Figure 2:
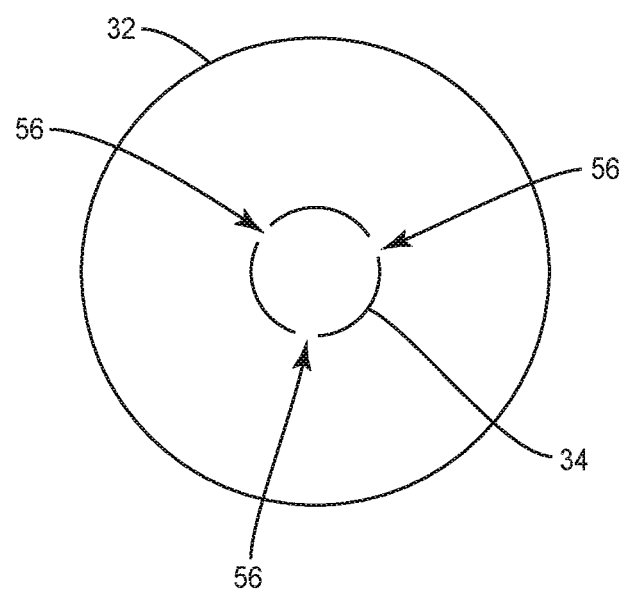
FIG. 2 is a cross sectional view of one embodiment of the surgical instrument shown in FIG. 1.

In some embodiments, shaft 34 has a non-porous, solid wall configuration (e.g., FIGS. 1 and 2) and includes one or a plurality of inflation ports 56 that each extend through a thickness of shaft 34 and are in communication with lumen 42. As the inflation material moves through lumen 42, the inflation material will exit lumen 42 through inflation ports 56 and enter chamber 54 to move balloon 32 from an uninflated configuration (e.g., FIG. 1) to an inflated configuration (e.g., FIG. 4). In some embodiments, shaft 34 includes a plurality of spaced apart inflation ports 56, as shown in FIG. 1. In some embodiments, inflation ports 56 are spaced apart from each other along a length of shaft 34 and/or are spaced apart radially about a circumference of shaft 34, as shown in FIG. 2. In some embodiments, shaft 34 includes only one inflation port 56, as shown in FIGS. 5-7. In some embodiments, inflation port(s) 56 may be variously shaped, such as, for example, oval, oblong, triangular, square, polygonal, irregular, uniform, non-uniform, offset, staggered, undulating, arcuate, variable and/or tapered.

In embodiments wherein shaft 34 is laser cut, braided, or coiled, the inflation material can enter chamber 54 through gaps or pores in shaft 34 that are not covered or encapsulated by polymer 40. For example, the gaps or pores may be defined by spaces between coils, as shown in FIG. 3. Likewise, the gaps or pores may be defined by spaces between interlaced strands that make up the braid, as shown in FIG. 4. As the inflation material moves through lumen 42, the inflation material will exit lumen 42 through the gaps or pores in shaft 34 and enter chamber 54 to move balloon 32 from the uninflated configuration to the inflated configuration.

Inflatable bone tamp 22 includes a channel 58 between shaft 24 and shaft 34. Channel 58 is defined by the inner surface of shaft 34 and the outer surface of shaft 34. Channel 58 is configured to allow the material within chamber 54 that is used to inflate balloon 32 to exit chamber 54 to move balloon 32 from the inflated configuration to the uninflated configuration and/or to reduce the pressure within chamber 54, as discussed herein. A valve 60 is positioned within channel 58, as best shown in FIGS. 5-7. Valve 60 includes a sleeve 62 that extends between an end 64 and an opposite end 66, as best shown in FIGS. 8-10. In some embodiments, end 64 defines a linear portion of sleeve 62 and end 64 defines a tapered portion of sleeve 62. End 66 flares outwardly from end 64 such that end 66 has a maximum diameter that is greater than a maximum diameter of end 64. In some embodiments, end 66 has a maximum diameter that is at least 25% greater than a maximum diameter of end 64. In some embodiments, end 66 has a maximum diameter that is at least 50% greater than a maximum diameter of end 64. In some embodiments, end 66 has a maximum diameter that is at least 75% greater than a maximum diameter of end 64. In some embodiments, end 66 has a maximum diameter that is at least 100% greater than a maximum diameter of end 64. Valve 60 includes an inner surface that defines a cavity 68. Ends 64, 66 each include an opening that is in communication with cavity 68 such that cavity 68 extends through end 64 and end 66. In some embodiments, sleeve 62 comprises a polymer, such as, for example, a low durometer polymer. In some embodiments, the polymer comprises thermoplastic polyurethane. In some embodiments, the polymer has a durometer between 55 Shore A and 70 Shore D. In some embodiments, sleeve 62 comprises an elastic material. In some embodiments, sleeve 62 comprises a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

Valve 60 is positioned relative to shaft 34 such that a portion of shaft 34 is positioned within cavity 68, as shown in FIGS. 5-7. In particular, shaft 34 is positioned within cavity 68 such that the inner surface of sleeve 62 directly engages the outer surface of shaft 34. In some embodiments, sleeve 62 is molded or otherwise coupled with shaft 34 such that sleeve 62 is permanently attached to shaft 34 and cannot be removed from shaft 34 without breaking and/or damaging sleeve 62 and/or shaft 34. In some embodiments, sleeve 62 is coupled to shaft 34 such that sleeve 62 is removable from shaft 34. This can allow sleeve 62 to be selectively positioned and/or repositioned along a length of shaft 34. In some embodiments, sleeve 62 has an inner diameter that is slightly greater than an outer diameter of shaft 34 to allow sleeve 62 to slide along shaft 34. In some embodiments, sleeve 62 has an inner diameter that is slightly less than an outer diameter of shaft 34 such that sleeve 62 must be stretched to be positioned about shaft 34 such that shaft 34 is positioned within cavity 68. It is envisioned that sleeve 62 will return to an unstretched configuration after the force used to stretch sleeve 62 is removed and that the inner surface of sleeve 62 will directly engage the outer surface of shaft 34 such that there is no spaced between shaft 34 and sleeve 62 when sleeve 62 is in the unstretched configuration. In some embodiments, the outer surface of shaft 34 and/or the inner surface of sleeve 62 may have various surface configurations, such as, for example, smooth and/or surface configurations to enhance fixation of sleeve 62 with shaft 34, such as, for example, rough, arcuate, undulating, porous, semi-porous, dimpled, polished and/or textured according to the requirements of a particular application. In some embodiments, sleeve 62 can be variously connected with shaft 34, such as, for example, monolithic, integral connection, frictional engagement, threaded engagement, mutual grooves, adhesive, barbs and/or raised element.

Valve 60 is configured to deform at a predetermined pressure to move valve 60 between a closed configuration in which valve 60 completely blocks channel 58 and an open configuration in which valve 60 does not completely block channel 58. When valve 60 is in the closed configuration, the inner surface of sleeve 62 directly engages the outer surface of shaft 34 and an outer surface of end 66 directly engages the inner surface of shaft 24 to form a seal between shaft 24 and shaft 34, as shown in FIG. 6. End 64 of sleeve 62 is spaced apart from the inner surface of shaft 24 when valve 60 is in the closed configuration. End 66 of sleeve 62 has a maximum diameter that is greater than a maximum diameter of end 64 when valve 60 is in the closed configuration. In some embodiments, the predetermined pressure is between about 40 psi and about 1,000 psi. In some embodiments, the predetermined pressure is about 50 psi, about 100 psi, about 200 psi, about 300 psi, about 400 psi, about 500 psi, about 600 psi, about 700 psi, about 800 psi, about 900 psi, or about 1000 psi. In some embodiments, the predetermined pressure is greater than 1,000 psi. In some embodiments, valve 60 is a one-way valve that allows material to move passed valve 60 in the direction shown by arrow A in FIG. 7, but does not allow material to be moved passed valve 60 in the direction shown by arrow B in FIG. 7 when valve 60 is in the open configuration. In some embodiments, valve 60 is a two-way valve that allows material to move passed valve 60 in the direction shown by arrow A in FIG. 7 and the direction shown by arrow B in FIG. 7 when valve 60 is in the open configuration.

When pressure within chamber 54 reaches a predetermined threshold, such as, for example, the predetermined pressure, the pressure will cause valve 60 to deform to move valve 60 from the closed configuration to the open configuration. When valve 60 is in the open configuration, the outer surface of end 66 is spaced apart from the inner surface of shaft 24 such that the material within chamber 52 can move through channel 58 in the direction shown by arrow A in FIG. 7 and passed valve 60 to reduce the pressure within chamber 54. In some embodiments, balloon 32 moves from the inflated configuration to the uninflated configuration as the material moves passed valve 60. End 66 of sleeve 62 has a maximum diameter when valve 60 is in the open configuration that is less than a maximum diameter of end 66 when valve 60 is in the closed configuration. In some embodiments, end 64 of sleeve 62 has a maximum diameter when valve 60 is in the open configuration that is equal or substantially equal to a maximum diameter of end 64 when valve 60 is in the closed configuration. In some embodiments, end 64 of sleeve 62 has a maximum diameter that is equal or substantially equal to a maximum diameter of end 66 when valve 60 is in the closed configuration.

In use, to treat a bone disorder, such as, for example, a spinal fracture, a medical practitioner obtains access to a target location including at least one vertebra, such as, for example, a fractured vertebra V, in any appropriate manner, such as through incision and retraction of tissue. It is envisioned that the balloon catheter system 20 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Figure 11:
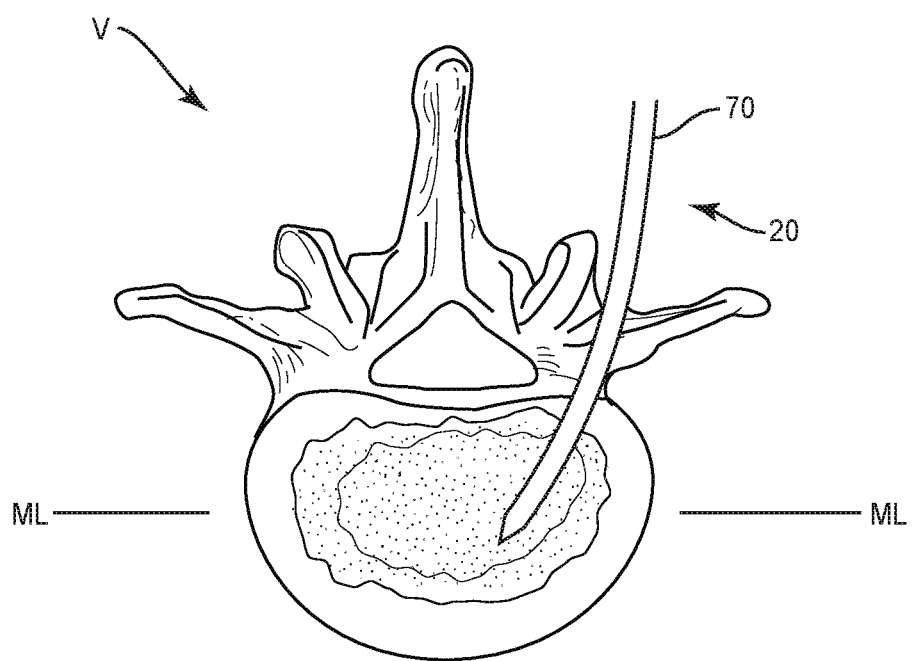
FIG. 11 is a plan view of a surgical instrument in accordance with the principles of the present disclosure being inserted into a vertebra.
Figure 12:
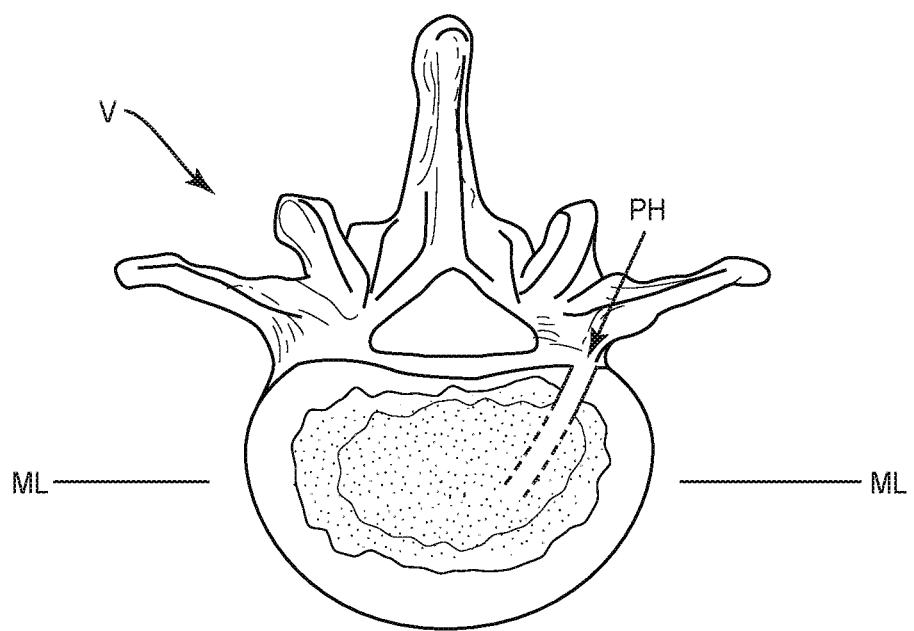
FIG. 12 is a plan view of the vertebra shown in FIG. 11.
Figure 13:
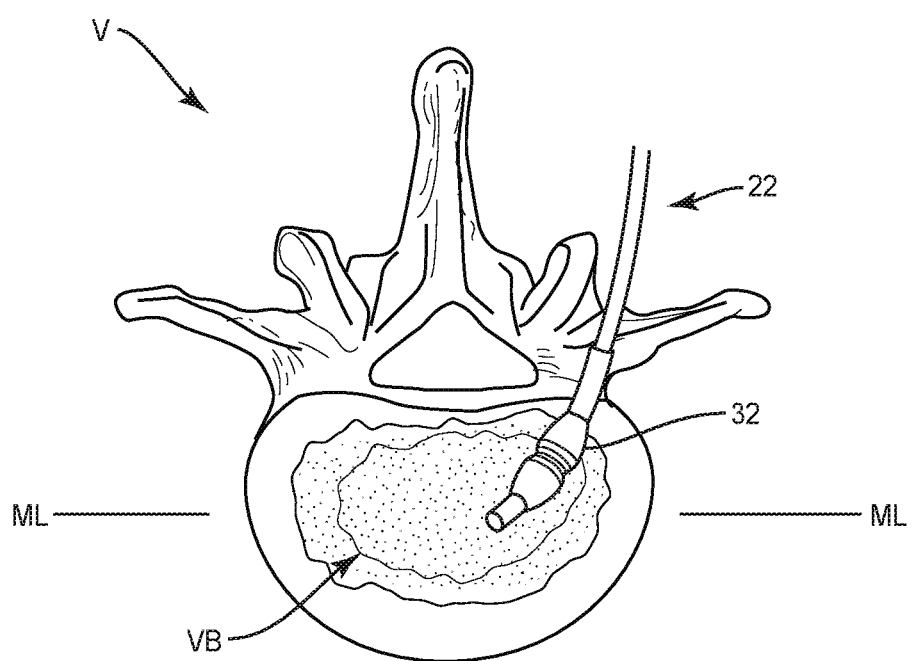
FIG. 13 is a plan view of the surgical instrument shown in FIG. 1 inserted into the vertebra shown in FIG. 11.
Figure 14:
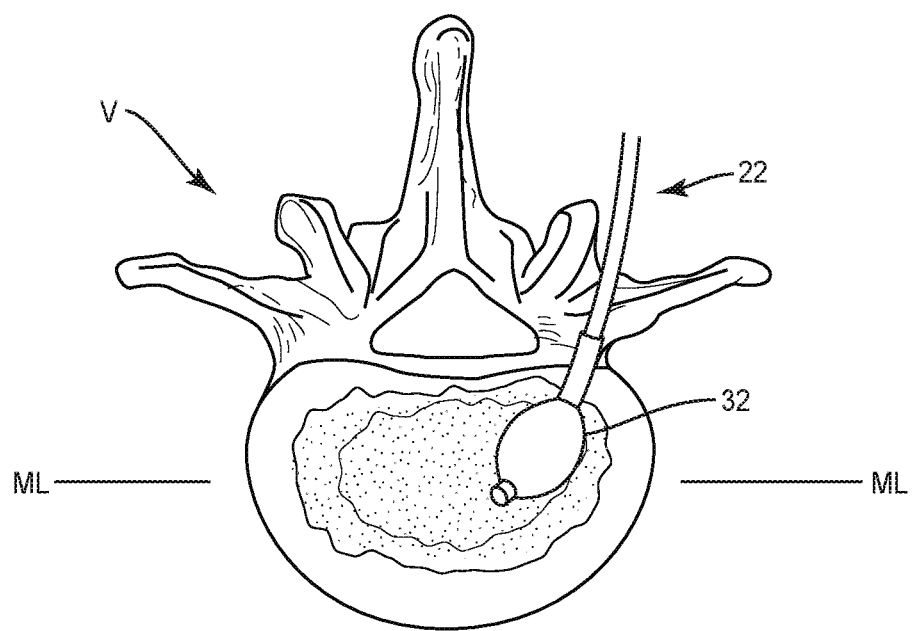
FIG. 14 is a plan view of the surgical instrument shown in FIG. 1 inserted into the vertebra shown in FIG. 11.

As shown in FIG. 11, balloon catheter system 20 includes a curved stylet 70 that is inserted through vertebra V and into a vertebral body VB of vertebra V to access vertebral body VB through a unipedicular approach and create a curved pilot hole PH, as shown in FIG. 12. Inflatable bone tamp 22 is inserted through pilot hole PH with balloon 32 in the uninflated configuration such balloon 32 is positioned within vertebral body VB, as shown in FIG. 13. Balloon 32 is moved from the uninflated configuration to the inflated configuration as discussed herein and shown in FIG. 14. Should pressure within chamber 54 of balloon 32 reach the predetermined threshold pressure as balloon moves from the uninflated configuration to the inflated configuration, valve 60 will move from the closed configuration to the open configuration to allow the material within chamber 54 that is being used to inflate balloon 32 to move through channel 58 in the direction shown by arrow A in FIG. 7 and passed valve 60 to reduce the pressure within chamber 54. Balloon 32 can then be inflated at a lower pressure until balloon 32 is fully inflated. Should pressure within chamber 54 of balloon 32 remain below the predetermined threshold pressure as balloon moves from the uninflated configuration to the inflated configuration, valve 60 will remain the closed configuration until balloon 32 is fully inflated.

Figure 15:
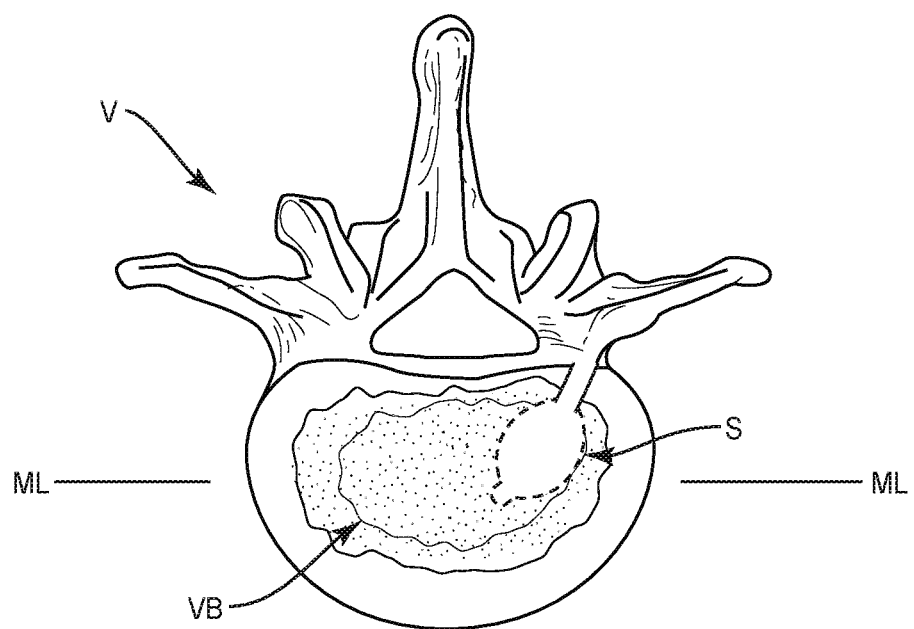
FIG. 15 is a plan view of the vertebra shown in FIG. 11.
Figure 16:
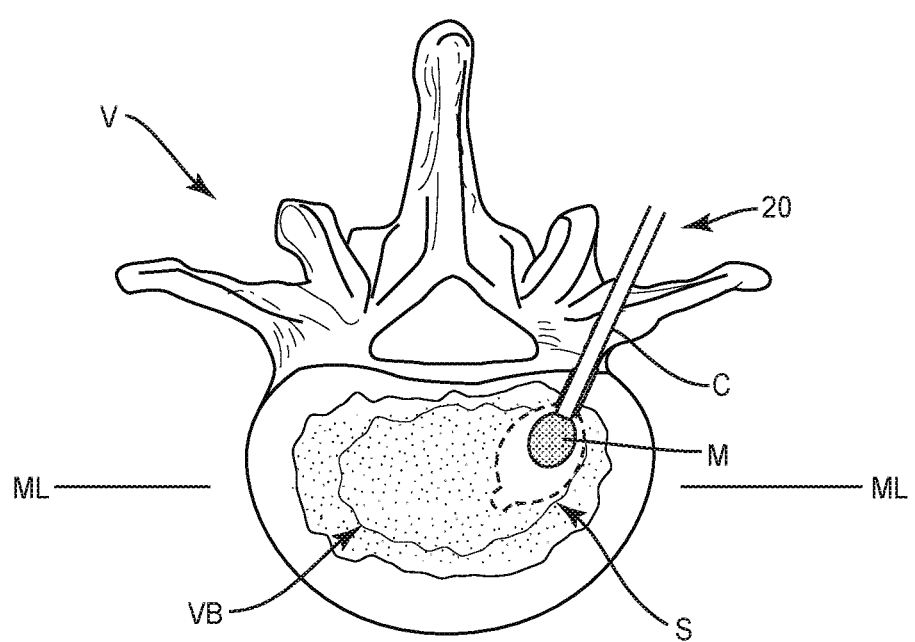
FIG. 16 is a plan view of a surgical instrument in accordance with the principles of the present disclosure being inserted into the vertebra shown in FIG. 11.

As balloon 32 moves from the uninflated configuration to the inflated configuration, balloon 32 creates a void, such as, for example, a space S within vertebral body VB, as shown in FIG. 15. Inflatable bone tamp 22 is removed from vertebra V and a cannula C of system 20 is inserted through pilot hole PH and into space S, as shown in FIG. 16. In some embodiments, balloon 32 is moved from the inflated configuration to the uninflated configuration prior to removing curved inflatable bone tamp 22 from vertebra V. In some embodiments, negative pressure, such as, for example, a vacuum is applied to lumen 42 to draw the inflation material out of lumen 42 and move balloon 32 from the inflated configuration to the uninflated configuration. A material, such as, for example, a bone filler material M is inserted through cannula C and into space S, as also shown in FIG. 16. Material M may be inserted into space S until material M fills all or a portion of space S. Cannula C is removed from vertebra V and material M is allowed to cure to treat the fracture by reducing pain from the fracture, stabilizing vertebra V and/or restoring vertebra V back to its normal height.

Figure 17:
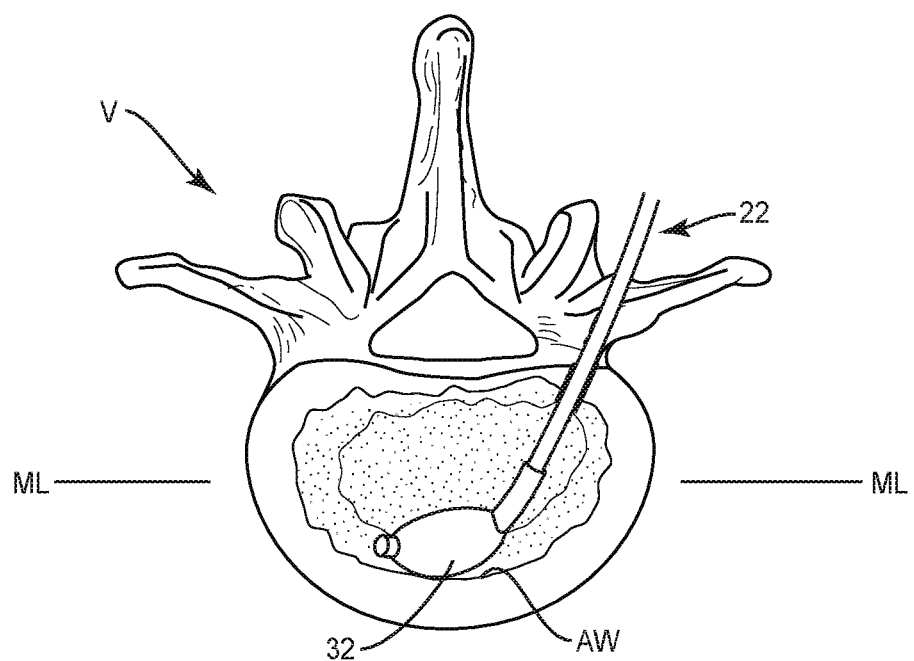
FIG. 17 is a plan view of the surgical instrument shown in FIG. 1 inserted into the vertebra shown in FIG. 11.
Figure 18:
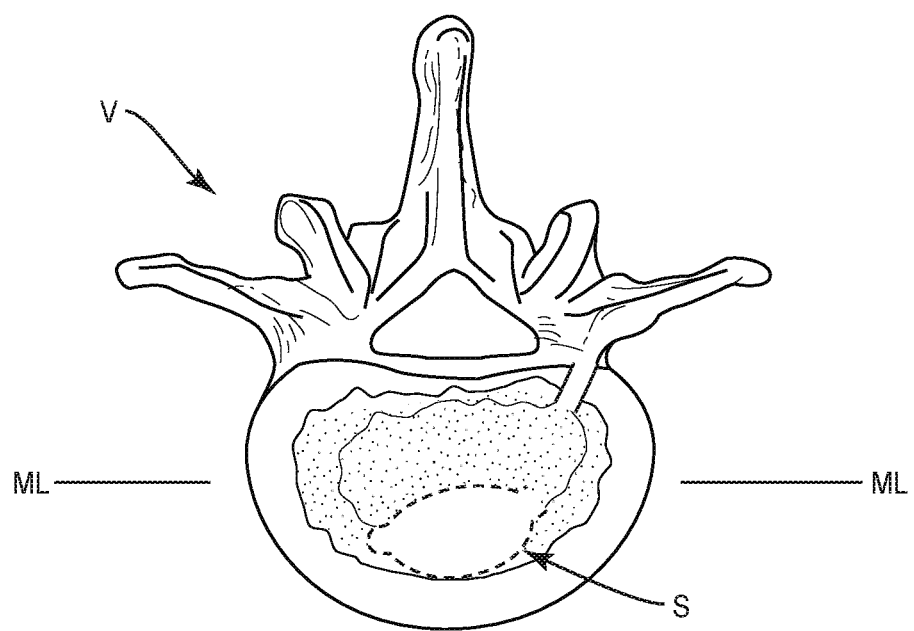
FIG. 18 is a plan view of the vertebra shown in FIG. 11.
Figure 19:
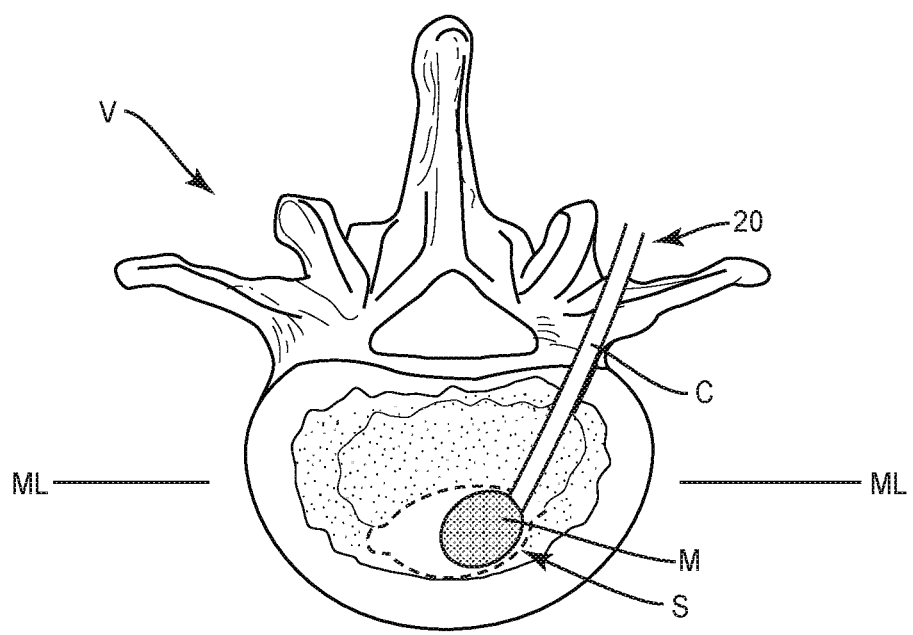
FIG. 19 is a plan view of a surgical instrument in accordance with the principles of the present disclosure being inserted into the vertebra shown in FIG. 11.

In some embodiments, pilot hole PH is oriented to position balloon 32 such that balloon 32 follows an anterior wall AW of vertebral body VB when balloon 32 is inflated within vertebral body VB, as shown in FIG. 17. As shown in FIG. 17, balloon 32 is positioned more anterior than posterior and extends passed midline M of vertebral body VB. In some embodiments, the size and shape of balloon 32 can be customized such that balloon 32 covers at least the anterior ⅔ of vertebral body VB to property treat a vertebral compression fracture of vertebra V. Balloon 32 is moved from the uninflated configuration to the inflated configuration to create space S within vertebral body VB, as shown in FIG. 18. Inflatable bone tamp 22 is removed from vertebra V and cannula C is inserted through pilot hole PH and into space S, as shown in FIG. 19. Material M is inserted through cannula C and into space S, as also shown in FIG. 19. Material M may be inserted into space S until material M fills all or a portion of space S.

In some embodiments, a kit containing one or more components of balloon catheter system 20 is provided. The kit may comprise components from any of the embodiments discussed herein. In some embodiments, the kit comprises one or more of the inflation materials discussed herein. In some embodiments, the kit comprises a plurality of cannulas, such as, for example, cannula C having different lengths configured for use with different size patients.

Figure 20:
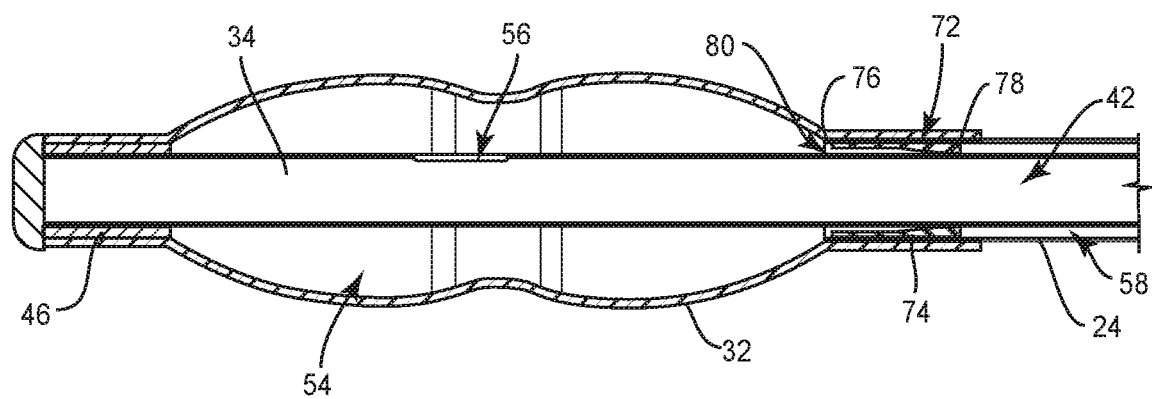
FIG. 20 is a side, cross sectional view of one embodiment of the surgical instrument shown in FIG. 1.
Figure 21:
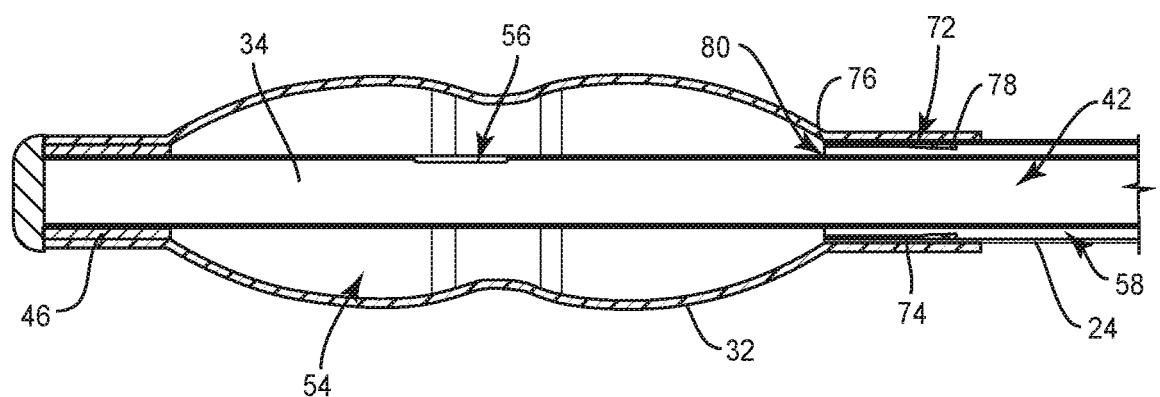
FIG. 21 is a side, cross sectional view of the surgical instrument shown in FIG. 20.

In one embodiment, shown in FIGS. 20 and 21, inflatable bone tamp 22 includes a valve 72 similar to valve 60. Valve 72 includes a sleeve 74 that extends between an end 76 and an opposite end 78. In some embodiments, end 76 defines a linear portion of sleeve 74 and end 78 defines a tapered portion of sleeve 74. End 78 is tapered inwardly from end 76 such that end 78 has a maximum inner diameter that is less than a maximum inner diameter of end 76. Valve 72 includes an inner surface that defines a cavity 80 similar to cavity 68. Ends 76, 78 each include an opening that is in communication with cavity 80 such that cavity 80 extends through end 76 and end 78. In some embodiments, sleeve 74 comprises a polymer, such as, for example, a low durometer polymer. In some embodiments, the polymer comprises thermoplastic polyurethane. In some embodiments, the polymer has a durometer between 55 Shore A and 70 Shore D. In some embodiments, sleeve 74 comprises an elastic material. In some embodiments, sleeve 74 comprises a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

Valve 72 is positioned relative to shaft 34 such that an outer surface of sleeve 74 directly engages the inner surface of shaft 24, as shown in FIGS. 20 and 21. In some embodiments, sleeve 74 is molded or otherwise coupled with shaft 24 such that sleeve 74 is permanently attached to shaft 24 and cannot be removed from shaft 24 without breaking and/or damaging sleeve 74 and/or shaft 24. In some embodiments, sleeve 74 is coupled to shaft 24 such that sleeve 74 is removable from shaft 24. This can allow sleeve 74 to be selectively positioned and/or repositioned along a length of shaft 24. In some embodiments, sleeve 74 has an outer diameter that is slightly less than an inner diameter of shaft 24 to allow sleeve 74 to slide along shaft 24. In some embodiments, sleeve 74 has an outer diameter that is slightly greater than an inner diameter of shaft 24 such that sleeve 74 must be compressed to be positioned within channel 58. It is envisioned that sleeve 74 will return to an uncompressed configuration after the force used to compress sleeve 74 is removed and that the outer surface of sleeve 74 will directly engage the inner surface of shaft 24 such that there is no spaced between shaft 24 and sleeve 74 when sleeve 74 is in the uncompressed configuration. In some embodiments, the inner surface of shaft 24 and/or the outer surface of sleeve 74 may have various surface configurations, such as, for example, smooth and/or surface configurations to enhance fixation of sleeve 74 with shaft 24, such as, for example, rough, arcuate, undulating, porous, semi-porous, dimpled, polished and/or textured according to the requirements of a particular application. In some embodiments, sleeve 74 can be variously connected with shaft 24, such as, for example, monolithic, integral connection, frictional engagement, threaded engagement, mutual grooves, adhesive, barbs and/or raised element.

Valve 72 is configured to deform at a predetermined pressure to move valve 72 between a closed configuration in which valve 72 completely blocks channel 58 and an open configuration in which valve 72 does not completely block channel 58. When valve 72 is in the closed configuration, the outer surface of sleeve 74 directly engages the inner surface of shaft 24 and an inner surface of end 78 directly engages the outer surface of shaft 34 to form a seal between shaft 24 and shaft 34, as shown in FIG. 20. End 76 of sleeve 74 is spaced apart from the outer surface of shaft 34 when valve 72 is in the closed configuration.

When pressure within chamber 54 reaches a predetermined threshold, such as, for example, the predetermined pressure, the pressure will cause valve 72 to deform to move valve 72 from the closed configuration to the open configuration. When valve 72 is in the open configuration, the inner surface of end 78 is spaced apart from the outer surface of shaft 34 such that the material within chamber 52 can move through channel 58 in the direction shown by arrow A in FIG. 7 and passed valve 72 to reduce the pressure within chamber 54. In some embodiments, balloon 32 moves from the inflated configuration to the uninflated configuration as the material moves passed valve 72.

Figure 22:
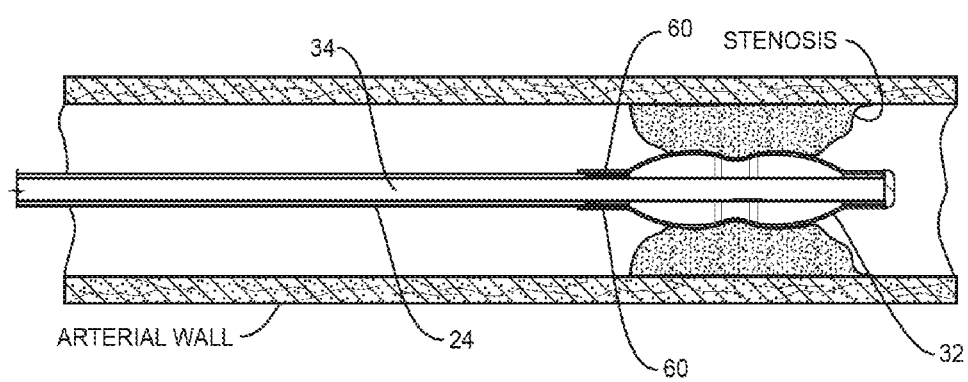
FIG. 22 is a longitudinal cross-sectional view of the surgical instrument shown in FIG. 1 inserted into an arterial stenosis.

It is envisioned that inflatable bone tamp 22 may be used in soft tissue spaces such as the vasculature, for example. For example, a medical practitioner can obtain access to a target location including an artery or vein in any appropriate manner. Inflatable bone tamp 22 is positioned within the artery or vein with balloon 32 in the uninflated configuration such that balloon 32 lies within an arterial stenosis, as shown in FIG. 22. Balloon 32 is then moved from the uninflated configuration to the inflated configuration to dilate the stenosis. While balloon 32 is in the inflated configuration, a catheter, such as, for example, a stent catheter is advanced over shaft 24. Balloon 32 is then moved from the inflated configuration to the uninflated configuration. A stent of the stent catheter is centered over balloon 32 such that the stent catheter cannot be advanced beyond balloon 32. Balloon 32 is then moved from the uninflated configuration to the inflated configuration, which causes the stent to be retained on balloon 32 when the stent catheter is pulled back. Balloon 32 is inflated until the stent is imbedded into stenotic plaque. Inflatable bone tamp 22 and the stent catheter are then removed from the artery. Should pressure within chamber 54 of balloon 32 reach the predetermined threshold pressure as balloon moves from the uninflated configuration to the inflated configuration, valve 60 will move from the closed configuration to the open configuration to allow the material within chamber 54 that is being used to inflate balloon 32 to move through channel 58 in the direction shown by arrow A in FIG. 7 and passed valve 60 to reduce the pressure within chamber 54. Balloon 32 can then be inflated at a lower pressure until balloon 32 is fully inflated. Should pressure within chamber 54 of balloon 32 remain below the predetermined threshold pressure as balloon moves from the uninflated configuration to the inflated configuration, valve 60 will remain the closed configuration until balloon 32 is fully inflated.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A bone tamp comprising:
a first shaft;
a second shaft extending through the first shaft, the first and second shafts defining a channel between the first shaft and the second shaft;
an inflatable member coupled to the first and second shafts; and
a valve positioned within the channel, the valve being configured to move from a closed orientation in which the valve blocks the channel and an open orientation in which the valve does not block the channel.

2. A bone tamp as recited in claim 1, wherein the inflatable member comprises a first end coupled to the first shaft and a second end coupled to the second shaft.

3. A bone tamp as recited in claim 1, wherein the bone tamp is configured such that material within the second shaft can flow through the second shaft and into the inflatable member when the valve is in the closed orientation.

4. A bone tamp as recited in claim 1, wherein the bone tamp is configured such that material within the inflatable member can exit the inflatable member through the channel when the valve is in the open orientation.

5. A bone tamp as recited in claim 1, wherein the bone tamp is configured such that material within the second shaft can flow through the second shaft and into the inflatable member when the valve is in the closed orientation and then exit the inflatable member through the channel when the valve is in the open orientation.

6. A bone tamp as recited in claim 1, wherein the channel is defined by an inner surface of the first shaft and an outer surface of the second shaft.

7. A bone tamp as recited in claim 1, wherein the channel is defined by an inner surface of the first shaft and an outer surface of the second shaft, the first shaft comprising an outer surface opposite the inner surface of the first shaft, an end of the inflatable member being coupled directly to the outer surface.

8. A bone tamp as recited in claim 1, wherein the channel is defined by an inner surface of the first shaft and an outer surface of the second shaft, the valve directly engaging the inner surface when the valve is in the closed orientation.

9. A bone tamp as recited in claim 8, wherein the valve is spaced apart from the inner surface when the valve is in the closed orientation.

10. A bone tamp as recited in claim 1, wherein the valve moves from the closed orientation to the open orientation when pressure within the inflatable member reaches a threshold pressure.

11. A bone tamp as recited in claim 1, wherein the valve includes a sleeve having a linear portion and a tapered portion, wherein the tapered portion directly engages an inner surface of the first shaft when the valve is in the closed orientation and is spaced apart from the inner surface when the valve is in the open orientation.

12. A bone tamp as recited in claim 1, wherein the valve comprises a polymer having a durometer between 55 Shore A and 70 Shore D.

13. A bone tamp as recited in claim 1, wherein the second shaft comprises a closed distal end, an end of the inflatable member being coupled to the closed distal end.

14. A bone tamp as recited in claim 1, wherein the second shaft comprises a super-elastic metallic material and the first shaft comprises a metallic material.

15. A bone tamp comprising:
a first shaft;
a second shaft extending through the first shaft, the first and second shafts defining a channel between the first shaft and the second shaft;
an inflatable member coupled to the first and second shafts; and
a valve positioned within the channel, the valve being configured to move from a closed orientation in which the valve blocks the channel and an open orientation in which the valve does not block the channel,
wherein the bone tamp is configured such that when then second shaft is inserted into the first shaft, the second shaft causes the first shaft to move from a straight configuration to a curved configuration.

16. A bone tamp as recited in claim 15, wherein the second shaft is pre-bent to be curved between opposite ends of the second shaft.

17. A bone tamp as recited in claim 15, wherein the second shaft includes a plurality of uniaxial laser cuts such that the second shaft is pre-bent to be curved between opposite ends of the second shaft.

18. A bone tamp as recited in claim 17, wherein a portion of the second shaft that includes the laser cuts is covered with a polymer.

19. A bone tamp as recited in claim 15, wherein the second shaft comprises a super-elastic metallic material and the first shaft comprises a metallic material.

20. A bone tamp comprising:
a first shaft;
a second shaft extending through the first shaft, the first and second shafts defining a channel between the first shaft and the second shaft, the second shaft comprising opposite first and second ends, the first end comprising a first opening, the second end comprising a second opening, the second shaft defining a lumen, the openings being in communication with the lumen;
a cap coupled to the second end such that the cap covers the second opening;
an inflatable member coupled to the first shaft and the cap; and
a valve positioned within the channel, the valve being configured to move from a closed orientation in which the valve blocks the channel and an open orientation in which the valve does not block the channel.

* * * * *